United States Patent [19]

Warren, III et al.

[11] Patent Number: 5,272,077
[45] Date of Patent: Dec. 21, 1993

[54] METHOD FOR PREPARING A COVALENT CONJUGATE OF AN OLIGONUCLEOTIDE AND AN ENZYME

[75] Inventors: Harold C. Warren, III, Rush; Fred T. Oakes, Rochester, both of N.Y.

[73] Assignee: Eastman Kodak Company, Rochester, N.Y.

[21] Appl. No.: 58,723

[22] Filed: May 10, 1993

Related U.S. Application Data

[60] Division of Ser. No. 762,136, Sep. 17, 1991, which is a continuation-in-part of Ser. No. 406,224, Sep. 12, 1989, Pat. No. 5,082,780.

[51] Int. Cl.$^5$ .................... C12N 9/96; C12N 9/04; C12N 9/06; C12N 9/08
[52] U.S. Cl. .................... 435/188; 435/190; 435/191; 435/192; 435/6; 435/91.1; 548/546; 548/544
[58] Field of Search ............... 435/188, 191, 190, 192, 435/6, 91; 548/546, 544

[56] References Cited

U.S. PATENT DOCUMENTS

| | | | |
|---|---|---|---|
| 4,510,246 | 4/1985 | Wolfe et al. | 435/191 |
| 4,536,476 | 8/1985 | Wolfe et al. | 435/191 |
| 4,711,964 | 12/1987 | Tan et al. | 548/546 |
| 4,914,210 | 4/1990 | Levenson et al. | 548/413 |
| 4,962,029 | 10/1990 | Levenson et al. | 435/192 |

FOREIGN PATENT DOCUMENTS

89/02932 4/1989 PCT Int'l Appl. .
89/06701 7/1989 PCT Int'l Appl. .

OTHER PUBLICATIONS

Connolly et al, *Nucl. Acids Res.*, 13(12), pp. 4485–4502 (1985).
Saiki et al, *N. Eng. J. Med.*, 319(9), pp. 537–541 (1988).
Coull et al, *Tetra. Lett.*, 27(34), pp. 3991–3994 (1986).
Jublonski et al, *Nucl. Acids Res.*, 14(15), pp. 6115–6126 (1986).
Connolly, *Nucl. Acids Res.*, 15(7), pp. 3131–3139 (1987).
Sproat et al, *Nucl. Acids Res.*, 15(15), pp. 6181–6196 (1987).
Ruth et al, *Nucleosides & Nucleotides*, 6(1&2), pp. 541–542, (1987).

*Primary Examiner*—David M. Naff
*Assistant Examiner*—Michael V. Meller
*Attorney, Agent, or Firm*—J. Lanny Tucker

[57] ABSTRACT

A method is provided for preparing a covalent conjugate of an oligonucleotide and an enzyme, such as peroxidase. This conjugate can be used as a probe in hybridization assays and in polymerase chain reaction procedures. The method generally comprises the steps of: reacting an enzyme having a reactive amino group with a mercapto-substituted organic compound to form a blocked intermediate, removing the blocking group to form an enzyme reagent, and reacting the enzyme reagent with a functionalized oligonucleotide reagent.

12 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:

(A) LENGTH: 23 nucleotides
(B) TYPE: Nucleic acid
(C) STRANDEDNESS: Single
(D) TOPOLOGY: Linear (ii) MOLECULE TYPE: Oligonucleotide (iii) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:1:

GAGTGATGAG GAAGAGGAGG GTG    23

(2) INFORMATION FOR SEQ ID NO:2:

(i) SEQUENCE CHARACTERISTICS:
(A) LENGTH: 29 nucleotides
(B) TYPE: Nucleic acid
(C) STRANDEDNESS: Single
(D) TOPOLOGY: Linear (ii) MOLECULE TYPE: Oligonucleotide (iii) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:2:

UTTTGGTCCT TGTCTTATGT CCAGAATGC    29

(2) INFORMATION FOR SEQ ID NO:3:

(i) SEQUENCE CHARACTERISTICS:
(A) LENGTH: 41 nucleotides
(B) TYPE: Nucleic acid
(C) STRANDEDNESS: Single
(D) TOPOLOGY: Linear (ii) MOLECULE TYPE: Oligonucleotide (iii) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:3:

TAGTAGCCAG CTGTGATAAA TGTCAGCTAA AAGGAGAAGC C    41

(2) INFORMATION FOR SEQ ID NO:4:

(i) SEQUENCE CHARACTERISTICS:
(A) LENGTH: 35 nucleotides
(B) TYPE: Nucleic acid
(C) STRANDEDNESS: Single
(D) TOPOLOGY: Linear (ii) MOLECULE TYPE: Oligonucleotide (iii) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:4:

ACGGTACAGG CCAGACAATT ATTGTCTGGT ATAGT    35

(2) INFORMATION FOR SEQ ID NO:5:

(i) SEQUENCE CHARACTERISTICS:
(A) LENGTH: 33 nucleotides
(B) TYPE: Nucleic acid
(C) STRANDEDNESS: Single
(D) TOPOLOGY: Linear (ii) MOLECULE TYPE: Oligonucleotide (iii) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:5:

GAGACCATCA ATGAGGAAGC TGCAGAATGG GAT    33

(2) INFORMATION FOR SEQ ID NO:6:

(i) SEQUENCE CHARACTERISTICS:
(A) LENGTH: 31 nucleotides
(B) TYPE: Nucleic acid
(C) STRANDEDNESS: Single
(D) TOPOLOGY: Linear (ii) MOLECULE TYPE: Oligonucleotide (iii) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:6:

ATCCTGGGAT TAAATAAAAT AGTAAGAATG T    31

METHOD FOR PREPARING A COVALENT CONJUGATE OF AN OLIGONUCLEOTIDE AND AN ENZYME

RELATED APPLICATION

This application is a divisional of U.S. Ser. No. 07/762,136, filed Sep. 17, 1991, which is a continuation-in-part of U.S. Ser. No. 406,224 filed Sep. 12, 1989, now U.S. Pat. No. 5,082,780.

FIELD OF THE INVENTION

This invention relates to a covalent conjugate of an oligonucleotide and an enzyme which is useful in DNA hybridization or the detection of polymerase chain reaction products. Also provided is a method for preparing this conjugate

BACKGROUND OF THE INVENTION

The use of single-stranded DNA or RNA probes to test for the presence of particular nucleic acids, and associated organisms and genetic features in biological materials is well known. Among areas in which such probes find usefulness include diagnostic testing of foods, blood and other biological specimens for infectious agents, diagnosis of genetic disorders and the presence of certain diseases such as cancers associated with genetic abnormalities. Non-isotopically labeled synthetic oligonucleotides are widely used in DNA sequencing, DNA hybridization assays, and more recently in amplification procedures, commonly known as polymerase chain reaction procedures described in U.S. Pat. Nos. 4,683,195 (issued Jul. 28, 1987 to Mullis et al) and 4,683,202 (issued Jul. 28, 1987 to Mullis).

The principle underlying the use of probes or primers is that under certain conditions, the probe or primer will hybridize by means of hydrogen bonding with a nucleic acid having complementary nucleotides. The hybridized product can then be suitably detected directly or after amplification procedures using appropriate reagents.

Early probes were labeled with radioisotopes such as $^{32}$P-labeled nucleotide triphosphates. However, they are unsuitable for many applications and are generally avoided due to safety and licensing considerations, and because of the natural decay of the label during storage.

Research has been continuing to find suitable labels for probes which do not have such disadvantages, as noted in EP-A-0 278 220 (published Aug. 17, 1988) and U.S. Pat. No. 4,780,405 (issued Oct. 25, 1988 to Kaiser et al). Enzyme labels have become the most generally used labels for labeled oligonucleotides, noted for example in EP-A-0 304 934 (published Mar. 1, 1989).

U.S. Ser. No. 103,978 (filed Oct. 2, 1987 by Levenson et al), now U.S. Pat. No. 4,962,029 (issued Oct. 9, 1990), describes the attachment of horseradish peroxidase to an oligonucleotide to form a covalent conjugate. In forming this conjugate, a mercapto-functionalized oligonucleotide is reacted with a maleimide-functionalized horseradish peroxidase. While this procedure represents an advance in the art, further improvements are desired to avoid undesirable side products, such as oxidation products of the mercapto-functionalized oligonucleotide, as well as the expensive and time-consuming preparative steps involved. Moreover, the thiol-functionalized oligonucleotide is unstable and has limited storage life. For maximum efficiency, it should be used as soon as it is prepared.

It would be highly advantageous, then, to have a method which would provide an enzyme-labeled oligonucleotide conjugate with improved yields and stability. It would also be desirable to be able to avoid side reactions of the critical oligonucleotide reagent.

SUMMARY OF THE INVENTION

The problems noted above regarding known methods are overcome with a method for preparing a covalent conjugate of an oligonucleotide and an enzyme comprising the steps of:

A. reacting an enzyme which has either a reactive amino group or a group that is convertible to a reactive amino group, with a blocked mercapto-substituted organic compound which is reactive with the reactive amino group through a condensation reaction, the organic compound having the structure:

R*-E-S-BLOCK wherein
R* is a group which is capable of reacting with the reactive amino group,
E is selected from the group consisting of $R^5$, $R^5$-X'-$R^6$, X''-$R^5$ and X''-$R^5$-X'-$R^6$, wherein $R^5$ and $R^6$ are independently alkylene or arylene, X' is oxy, thio or imino, and X'' is carbonyl, methylenecarbonyl, methylenecarbonyloxy, methylenecarbonylimino, ethylenesulfonyl, ethylenecarbonyl and methylenephenylene, and E has a molecular weight of from about 14 to about 1000, and
BLOCK is derived from a compound which is capable of reacting with the mercapto group to render the mercapto group non-nucleophilic, which BLOCK is subsequently removable, to form intermediate A' having the structure:

X—NH—E—S—BLOCK wherein X—NH— is the enzyme with a hydrogen atom removed from a reactive amino group, B. removing BLOCK from intermediate A' to form a reagent having the structure:

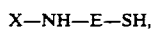

X—NH—E—SH,

C. providing an activated oligonucleotide derivative having the structure:

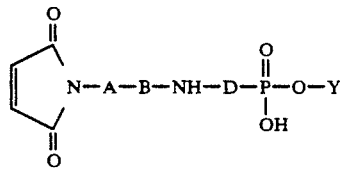

wherein:
A is selected from the group consisting of alkylene, arylene, cycloalkylene, heterocyclylene, and any combination of two or more of the foregoing divalent groups,
B is selected from the group consisting of carbonyl, sulfonyl, iminocarbonyl, oxycarbonyl, thiocarbonyl and phospho, D is —D'—(—B'—)p— wherein D' is selected from the group consisting of heterocyclylene, $R^7$—(—O—$R^8$—)q— wherein $R^7$ and $R^8$ are independently alkylene or arylene, and any combination of two or more of the foregoing divalent groups, B' is selected from the group consisting of oxy, thio, imino, carbonylimino, iminocarbonyloxy, phosphonoxy and ureylene, p is 0 or 1, q is 1 to 30, and

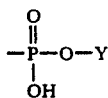

represents an oligonucleotide chain from which a hydroxy group has been removed from the terminal phosphate at the 3' or 5' end thereof, provided that —A—B—NH—D— has a molecular weight of from about 100 to about 10,000, and D. reacting the activated oligonucleotide derivative provided in step C with the reagent formed in step B to form a conjugate having the structure:

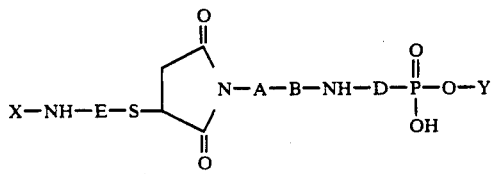

wherein A, B, D, E, X—NH—, and

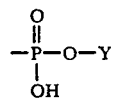

are as defined above.

This invention also provides a covalent conjugate of an enzyme and an oligonucleotide having the structure:

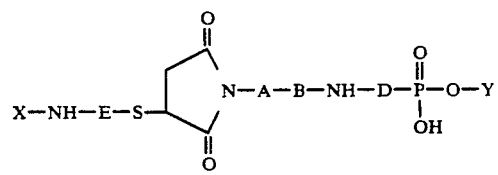

wherein

X—NH— represents an enzyme which has either a reactive amino group or a group which is convertible to a reactive amino group, from which a hydrogen atom has been removed from said reactive amino group, A is selected from the group consisting of alkylene, arylene, cycloalkylene, heterocyclylene, and any combination of two or more of the foregoing divalent groups, B is selected from the group consisting of carbonyl, sulfonyl, iminocarbonyl, phospho, oxycarbonyl and thiocarbonyl, D is —D'——(—B'—)p— wherein D' is selected from the group consisting of heterocyclylene, $R^7$—(—O—$R^8$—)q— wherein $R^7$ and $R^8$ are independently alkylene or arylene, and any combination of two or more of the foregoing divalent groups, B' is selected from the group consisting of oxy, thio, imino, carbonylimino, iminocarbonyloxy, phosphonoxy and ureylene, p is 0 or 1, q is 1 to 30, E is selected from the group consisting of and $R^5$, $R^5$—X'—$R^6$, X"—$R^5$ and X"—$R^5$—X'—$R^6$ wherein $R^5$ and $R^6$ are independently alkylene or arylene, X' is oxy, thio or imino and X" is carbonyl, methylenecarbonyl, methylenecarbonyloxy, methylenecarbonylimino, ethylenesulfonyl, ethylenecarbonyl and methylenephenylene, E has a molecular weight of from about 14 to about 1000, and

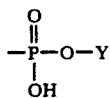

represents an oligonucleotide chain from which a hydroxy group has been removed from the terminal phosphate at the 3' or 5' end thereof, provided that —A—B—NH—D— has a molecular weight of from about 100 to about 10,000.

This invention provides a simplified and rapid means for making an enzyme-labeled oligonucleotide conjugate for use in DNA or RNA assays or amplification procedures. Higher yields of the oligonucleotide-enzyme conjugate are obtained using the procedure of this invention. Also, the activated oligonucleotide derivative, considered the most important reagent in the method, is conserved. This is significant because its preparation is time-consuming and expensive. The production of unwanted side reactions by oxidation is also reduced. The enzyme having a reactive amino group can be converted to a thiol derivative by a simple and inexpensive procedure. This reagent can be used in excess because loss of the reagent by any side reactions is not as critical.

These advantages are achieved by avoiding the use of a thiol-substituted oligonucleotide according to the teaching of U.S. Pat. No. 4,962,029 (noted above). Rather, a reactive thiol group is added to a derivatized enzyme, then reacted with an activated oligonucleotide derivative.

DETAILED DESCRIPTION OF THE INVENTION

As used herein, the term "mercapto-derivatized" refers to a blocked (that is, protected) mercapto group. The mercapto group is spaced apart from the enzyme moiety of the resulting reagent by an organic spacer chain as described herein.

A "blocked" mercapto group refers to one which is protected from chemical reaction while a "blocking" group is present. Such a "blocking" group is subsequently removed or cleaved to allow reaction of the mercapto group.

An oligonucleotide is a single- or double-stranded chain of nucleotides, generally deoxyribonucleotide monomer units. While the reagents and method of the present invention can conceivably be used with a single nucleotide monomer or with a complete DNA molecule, the oligonucleotides used herein are generally single-stranded and have from about 10 to 100 nucleotides. Optimal length of the oligonucleotide will vary depending upon the use of the resulting conjugate.

The covalent conjugate provided by this invention has the general structure (I):

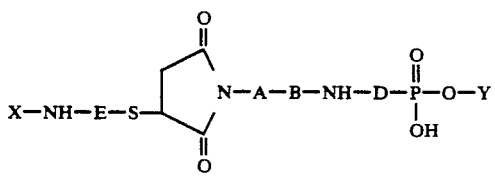

wherein X—NH— represents an enzyme which has either a reactive amino group or a group capable of being converted to a reactive amino group, from which reactive amino group a hydrogen atom has been removed. By "reactive amino group" is meant an amino group which is available and readily reactive with an appropriate reagent (described below).

Enzymes naturally having reactive amino groups can be used in the practice of this invention, and include, but are not limited to, peroxidase, glucose oxidase, alkaline phosphatase, β-galactosidase and urease. The first four enzymes are preferred with peroxidase being most preferred.

Alternatively, the enzyme may be chemically modified in some manner (that is, converted) to provide a reactive amino group. This must be done, however, in such a manner as to keep the enzyme moiety reactive with the appropriate substrate so the enzyme will remain suitably detectable and retain its activity.

The enzyme is linked to a succinimide moiety that is,

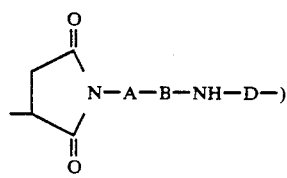

in the conjugate through —E—S— which represents a divalent organic moiety derived from a mercapto-substituted organic compound which is capable of reaction with the reactive amino group of the enzyme. Thus, the protected mercapto-substituted organic compound has one or more reactive groups such as activated carboxy, anhydride, activated ester or acid halide groups.

The group E can represent any suitable divalent organic moiety having divalent aliphatic (straight chain, branched or saturated carbocyclic), aromatic (such as phenylene) or heterocyclic groups in the chain which can be interrupted or terminated with one or more carbonyl, oxy or other non-hydrocarbon moieties as used below to define B. Generally, E has a molecular weight in the range of about 14 to about 1,000.

More preferably, E is selected from the group consisting of $R^5$, $R^5$—X'—$R^6$, X"—$R^5$ and X"'—$R^6$—X-'—$R^6$ wherein $R^5$ and $R^6$ are independently substituted or unsubstituted alkylene (generally of from 1 to 10 carbon atoms, such as methylene, ethylene, isopropylene, methoxyethylene, butylene, t-butylene, hexylene, 2-carboxyethylene and decylene), or substituted or unsubstituted arylene (generally of from 6 to 14 carbon atoms in the aromatic ring, such as phenylene, naphthylene, 2-methylphenylene and anthranylene). In the formula $R^5$—X'—$R^6$, $R^5$ and $R^6$ can be the same or different, and X' is oxy, thio or imino. Representative of such groups include, but are not limited to substituted or unsubstituted alkyleneoxyalkylene (each alkylene being independently of from 1 to 4 carbon atoms as defined above), substituted or unsubstituted alkylenethioalkylene (each alkylene being independently of from 1 to 4 carbon atoms as defined above), substituted or unsubstituted alkyleneoxyarylene (wherein alkylene and arylene are as defined above), substituted or unsubstituted aryleneoxyalkylene (wherein alkylene and arylene are as defined above), substituted or unsubstituted alkyleneaminoalkylene (such as ethyleneaminomethylene, methyleneaminoisopropylene and methyleneaminomethylene) and substituted or unsubstituted aryleneaminoalkylene (such as , phenyleneaminomethylene, phenyleneaminoethylene and phenyleneaminohexylene). Moreover, X" can be carbonyl, methylenecarbonyl, methylenecarbonyloxy, methylenecarbonylimino, ethylenesulfonyl, ethylenecarbonyl and methylenephenylene. Representative X"—$R^5$—X'—$R^6$ would be readily apparent to one skilled in the art. Any of these groups can be substituted with one or more groups such as lower alkyl (1 to carbon atoms), lower alkoxy (1 to 4 carbon atoms), halo (fluoro, bromo and chloro), carboxy, sulfonoxy and others readily apparent to one skilled in the art.

More preferably, the group E-S-BLOCK is a mercapto-protected alkylene anhydride wherein alkylene is as defined above. Most preferably, E is derived from an S-acetyl mercapto-substituted anhydride, such as S-acetyl mercaptosuccinic anhydride In structure (I) above defining the conjugate of this invention, A is selected from the group consisting of substituted or unsubstituted alkylene (generally as defined above), substituted or unsubstituted arylene (generally as defined above), substituted or unsubstituted cycloalkylene (generally of 5 to 8 carbon atoms in the ring, such as cyclopentylene, cyclohexylene, 3-methylhexylene, cyclohexylmethylene and cyclopentylmethylene), substituted or unsubstituted heterocyclylene (generally having from 5 to 8 atoms in the ring with at least one atom being sulfur, oxygen, nitrogen or selenium), and any combination of two or more of the foregoing divalent groups. Any of these divalent groups can be substituted with one or more substituents such as lower alkyl (1 to 4 carbon atoms), lower alkoxy (1 to 4 carbon atoms), halo (such as fluoro, cloro and bromo), carboxy, sulfonoxy, phosphonoxy and others readily apparent to one skilled in the art.

Preferably, A is a combination of two or more of any of the groups defined above, and more preferably, it is substituted or unsubstituted alkylenecycloalkylene of 7 to 14 carbon atoms in the backbone (such as methylenecyclohexylene, ethylenecyclohexylene and propylenecyclohexylene). Most preferably, A is methylenecyclohexylene.

In the foregoing structure (I) of the conjugate, B is defined generally as a linking group selected from the group consisting of carbonyl, sulfonyl, oxycarbonyl, thiocarbonyl, iminocarbonyl and phosphonyl. More preferably, B is carbonyl or oxycarbonyl with carbonyl being most preferred.

Further, D is defined as —D'——(—B'—)p-wherein D' is generally selected from the group consisting of substituted or unsubstituted heterocyclylene (as defined above), $R^7$—(—O—$R^8$-)q, and any combination of two or more of the foregoing divalent groups. $R^7$ and $R^8$ are the same or different and are independently alkylene or arylene as defined above. These groups can be substituted with any of the substituents defined above for A.

B' is a linking group selected from oxy, thio, imino, carbonylimino, iminocarbonyloxy, phosphonoxy and ureylene. Also, p is 0 or 1, and q is 1 to 30.

In preferred embodiments, B' is oxy or thio, p is 1, q is 1 to 15, and D' is $R^7$—(—O—$R^8$—)q-. In most preferred embodiments, B' is oxy and D' is —D"—(—oxalkylene—)q- wherein D" is substituted or unsubstituted alkylene of 1 to 6 carbon atoms and the alkylene of the oxyalkylene group is substituted or unsubstituted and has 2 to 12 carbon atoms (such as ethylene, isopropylene, hexylene and dodecylene).

In structure (I) noted above, the combined radicals represented by —A—B—NH—D— has a molecular weight of from about 100 to about 10,000, and preferably of from about 800 to about 4,000.

In the structure (I) above,

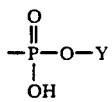

represents an oligonucleotide chain from which a hydroxy group has been removed from the terminal phosphate at the 3' or 5' end thereof. Preferably, the hydroxy group has been removed from the 5' end. Any oligonucleotide can be so attached for use as a probe, primer or other enzyme-labeled molecule for analytical, therapeutic or sequencing purposes.

Preferably, the covalent conjugate of this invention has the structure:

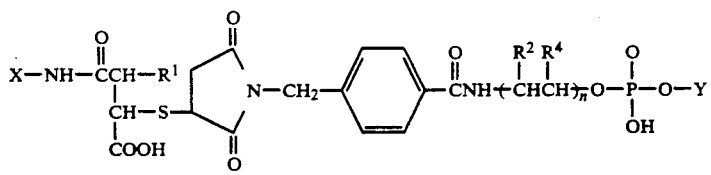

wherein
X—NH— represents an enzyme as defined above,
$R^1$, $R^2$, $R^3$ and $R^4$ are independently hydrogen, alkyl of 1 to 3 carbon atoms (such as methyl, ethyl, n-propyl or isopropyl) or hydroxyalkyl of 1 to 3 carbon atoms (hydroxymethyl, 2-hydroxyethyl and others apparent to one skilled in the art), m is a positive integer of 2 to 12, n is a positive integer of 1 to 50, and

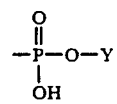

represents an oligonucleotide chain from which a hydroxy group has been removed as defined above.

More preferably, in the foregoing structure, $R^1$, $R^2$, $R^3$ and $R^4$ are independently hydrogen, methyl or hydroxymethyl, m is 2 and n is 1 to 15.

In one preferred conjugate, the enzyme is peroxidase, the oligonucleotide has the sequence:

SEQ ID NO:1:5'-GAGTGATGAG
GAAGAGGAGG GTG-3', $R^1$, $R^2$, $R^3$ and $R^4$ are each hydrogen, m is 2 and n is 1 to 15. A particularly useful conjugate has the structure:

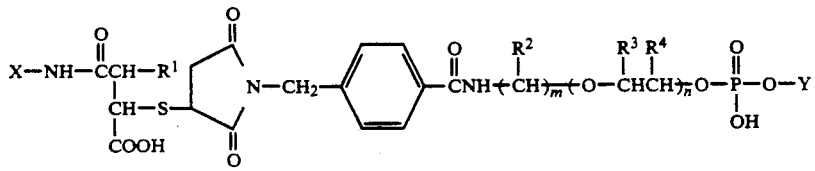

wherein X—NH— is from peroxidase, and

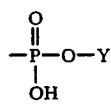

are as defined immediately above.

The conjugate of this invention is prepared using a series of steps which involves reacting derivatized enzymes and oligonucleotides with linking moieties by means of various intermediates which have desired stability, are produced in good yields and do not give unwanted side products.

In the first step of the method of this invention, an enzyme having a reactive amino group (as defined above) is reacted with a blocked (or protected) mercapto-substituted organic compound Alternatively, if the enzyme does not have the necessary reactive amino group, it can have a group which is convertible to a reactive amino group. The mercapto group is blocked so it will not prematurely react during this step. The organic compound has the structure:

R*—E—S—BLOCK wherein R* is a group which is capable of reacting with the reactive amino group In some instances, a portion of R* leaves the organic compound upon condensation. In other instances, it does not leave the compound, but may be removed from the site which is active in the reaction with the amino group (such as in the case of an anhydride ring opening).

Representative examples of R* include, but are not limited to, active halogen (such as haloacetyl, haloacetoxy, haloacetamido and halomethylphenyl), sulfonates (such as p-toluenesulfonate, p-bromobenzenesulfonate, p-nitrobenzenesulfonate, or methanesulfonate), —OCOR [wherein R is an aliphatic (such as methyl, ethyl, isopropyl or pentyl), aromatic (such as phenyl or tolyl) or a heterocyclic group (such as pyridyl)], carboxylic acid, chloroethylsulfonyl, vinylsulfonyl, chloroethylcarbonyl, acryloyl, and anhydrides (such as acetic, benzoic, succinic and phthalic anhydrides). Preferably, R* is an, anhydride, and most preferably, an aliphatic cyclic anhydride having up to 6 atoms in the ring.

The divalent E group is defined above.

The BLOCK group is derived from a compound which is capable of reacting with a mercapto group, rendering the mercapto group inactive until BLOCK has been removed in some manner. Representative BLOCK moieties include, but are not limited to, —COR' wherein R' represents an aliphatic (linear, branched or cyclic), aryl or heterocyclic group having a molecular weight of from about 15 to about 200, such as methyl, ethyl, phenyl or pyridyl. Other useful -BLOCK groups are pyridylthio, 2-carboxy-4-nitrophenylthio, triphenylmethyl or benzoyl. Preferably, -BLOCK is —COR' wherein R' is methyl (that is, acetyl) or phenyl.

Reaction of the organic compound and an enzyme as defined herein is carried out generally under atmospheric pressure at temperatures and for a time sufficient to obtain suitable yield of the resulting intermediate having the structure:

X—NH—E—S—BLOCK wherein X—NH— is the enzyme with a hydrogen atom removed from a reactive amino group. Generally, the temperature is in the range of from about 0 to about 37° C. and suitable pH conditions are in the range of from about 6 to about 9. These conditions will vary, however, depending upon the enzyme and the organic compound used. For instance, the pH and temperature must be suitable for the enzyme to remain active. The organic compound is at least partially soluble or dispersible in water, or provided in a water-miscible solvent to facilitate dispersion and reaction with the enzyme. Such a solvent must be used in quantities which will not interfere with enzyme reactivity.

The resulting intermediate, however, is not useful as such because of the blocking group attached to the thio group. It is subsequently removed to form a reactive reagent of the structure:

X—NH—E—SH, wherein X—NH— and E are defined above. Removing the blocking group is generally accomplished by treating the preferred compound with a solution of hydroxylamine and phosphate buffer (pH 7.4) containing ethylenediaminetetraacetic acid. Other conditions for removing a specific blocking group would be readily apparent to one skilled in the art.

An activated oligonucleotide derivative is then provided for reaction. This derivative has the general structure:

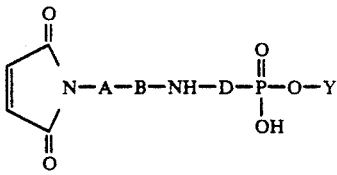

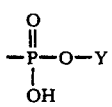

are as defined above.

This activated oligonucleotide derivative can be provided by following the teaching of U.S. Pat. No. 4,962,029 (noted above). Generally, the conditions of preparing these materials are as follows. An appropriate aminoethylene glycol reagent (with desired chain length) is reacted with phthalic anhydride without solvent at about 200° C. The resulting product is then reacted with a phosphine reagent in methylene chloride at 20°–25° C. This product is then reacted with an appropriate oligonucleotide attached to controlled pore glass using an automated synthesizer (commercially available) and standard procedures to form a derivatized oligonucleotide having a free amino group. The derivatized oligonucleotide is reacted with sulfosuccinimidyl 4-(N-maleimidomethyl)cyclohexane-1-carboxylate to form the activated oligonucleotide derivative illustrated above.

Lastly, the activated oligonucleotide derivative is reacted with the unblocked enzyme reagent to form the desired conjugate. Reaction conditions for this reaction are generally at about 4° C. in phosphate buffered saline solution (pH 7.4) for about 15 hours although these conditions may be varied for different reagents.

In a preferred embodiment, a method for preparing a covalent conjugate of an oligonucleotide and an enzyme comprises the steps of:

A. reacting an enzyme having a reactive amino group with S-acetylmercaptosuccinic anhydride to form an intermediate having the structure:

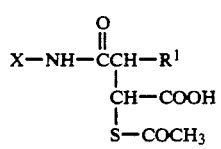

wherein
X—NH— represents an enzyme which has a reactive amino group from which a hydrogen atom has been removed, and R¹, is hydrogen, alkyl of 1 to 3 carbon atoms or hydroxyalkyl of 1 to 3 carbon atoms (these groups as defined above), B. reacting the intermediate formed in step A with hydroxylamine to form a reactive mercaptosubstituted intermediate having the structure:

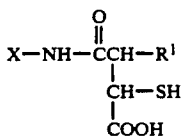

wherein X—NH— and R¹ are as defined above,

C. providing a functionalized oligonucleotide reactant having the structure:

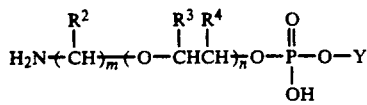

wherein

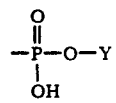

represents an oligonucleotide chain from which a hydroxy group has been removed from the terminal phosphate at the 5' end thereof, $R^2$, $R^3$ and $R^4$ are independently hydrogen, alkyl of 1 to 3 carbon atoms or hydroxyalkyl of 1 to 3 carbon atoms, m is a positive integer of 2 to 12 and n is a positive integer of 1 to 30, D. reacting the reactant provided in step C with sulfosuccinimidyl 4-(N-maleimidomethyl)cyclohexane-1-carboxylate to form an activated oligonucleotide derivative, and E. reacting the activated oligonucleotide derivative formed in step D with the intermediate formed in step B to form a conjugate having the structure:

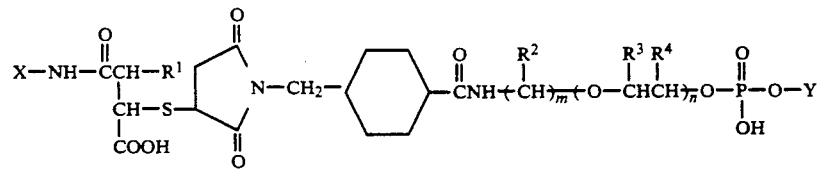

wherein X—NH—, $R^1$, $R^2$, $R^3$, $R^4$, m, n and

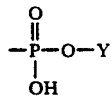

are as defined above.

In this embodiment, most preferably, each of $R^1$, $R^2$, $R^3$ and $R^4$ is hydrogen, m is 2, n is 1 to 15, and X—NH— is derived from peroxidase.

The specific conditions for carrying out this preferred embodiment are described in detail in the illustrative Examples below. However, it should be understood that other embodiments using other reagents would similarly be possible using the general conditions described above. Thus, the examples are not to be considered limiting.

EXAMPLE 1: PREPARATION OF PEROXIDASE OLIGONUCLEOTIDE CONJUGATE

A conjugate having horseradish peroxidase covalently attached to a single-stranded oligonucleotide was prepared in this example.

Materials

Various reagents were obtained commercially as follows: horseradish peroxidase from Sigma Chemical Company, S-acetylmercaptosuccinic anhydride from Aldrich Chemical Company, sulfosuccinimidyl 4-(N-maleimidomethyl)cyclohexane-1-carboxylate from Pierce Chemical Company, aminotriethyleneglycol from Texaco, chloro-2-cyanoethoxy-N,N-diisopropylaminophosphine from American Bionetics (Hayward, California), and all other reagents from Eastman Kodak Company or Aldrich Chemical Company.

The oligonucleotide used in this example had the sequence shown below where A, T, G and C represent the four standard deoxyribonucleoside triphosphate components: SEQ ID NO: 1:

5'-GAGTGATGAG GAAGAGGAGG GTG-3' and was attached to —A—B—NH—D— through its 5' hydroxyl group.

Various materials and equipment were obtained as follows: Biosearch 8700 DNA Synthesizer from Milligen/Biosearch, controlled pore glass support from Biosearch, SPECTROPOR ™ 2 dialysis bag from Spectrum Medical Industries (Los Angeles, Cal.), stirred cell concentrator from Amicon (Danvers, Massachusetts), PD-10 and NAP-10 columns from Pharmacia (Uppsala, Sweden), and a DEAE-agarose column from Waters.

PREPARATION

Step 1: Preparation of Mercapto-Substituted Enzyme Reagent

Horseradish peroxidase (100 mg dry weight) was dissolved in sodium carbonate (13.4 ml, 0.1 molar, pH 9.5) at 4° C. and reacted with a solution of S-acetylmercaptosuccinic anhydride in dry N,N-dimethylformamide (300 ml at 17.4 mg/ml) for one hour at 4° C. or lower. This mixture was transferred by pipette into a SPECTROPOR ™ 2 dialysis bag that had been prewet with deionized distilled water for 10 minutes. The bag was then placed into phosphate buffered saline solution (pH 7.4) using 50 times the volume of the reaction mixture, and slowly stirred at 4° C. for about four hours. The solution volume was concentrated using an Amicon concentrator to give 20–30 mg/ml of the desired intermediate.

This intermediate (1.34 ml of solution containing 41.85 mg/ml of phosphate buffered saline solution, pH 7.4) was unblocked by reaction with a solution containing hydroxylamine (1.2 ml, 0.25 molar) in phosphate buffer (0.1 molar, pH 7.4), and ethylenediaminetetraacetic acid (0.001 molar) for two hours at 20°–25° C. The resulting product was purified by chromatography using a PD-10 column and phosphate buffered saline solution (pH 7.4) as the eluent. The product (about 54 mg) was then used immediately in Part 3 below.

Part 2: Preparation of Activated Oligonucleotide Derivative

Aminotriethylene glycol (100 g) and phthalic anhydride (100 g) were mixed together and heated neat with stirring under nitrogen to 205° C., then cooled to room temperature. The resulting product was obtained as an oil which slowly solidified. The material was recrystallized from ethyl acetate (250 ml) to give 118 g of white crystalline product. The structure was confirmed by nuclear magnetic resonance spectroscopy.

This product (5 g) was dissolved in methylene chloride (50 ml), N,N-diisopropylethylamine (3 equivalents, 9.3 ml) was added, followed by chloro-2-cyanoethoxy-N,N-diisopropylaminophosphine (1.1 equivalents, 4.65 g) and the mixture was stirred at 20°-25° C. for 30 minutes. The reaction mixture was extracted with ethyl acetate (twice with 50 ml) and washed twice with water (50 ml), and concentrated using a rotary evaporator to give an oil (8.1 g). The material was 95% pure by nuclear magnetic resonance and mass spectral analysis. It was used as is in the next step. This product (500 ml of a solution of 4 g/70 ml of acetonitrile) was reacted with an oligonucleotide identified above (1 mmolar) in acetonitrile using the automated synthesizer, controlled pore glass and the procedures identified above. The last step consisted of hydrolysis with ammonium hydroxide to remove the oligonucleotide from the controlled pore glass and to unblock the amine to form an amino-derivatized, oligonucleotide reagent.

This reagent (OD 55 at 260 nm) was dissolved in deionized distilled water (500 ml) and cooled to 4° C. Sodium carbonate (50 ml of 1 molar solution, pH 8) was added to buffer the reaction. Sulfosuccinimidyl 4-(N-maleimidomethyl)cyclohexane-1-carboxylate (11.25 mg in 100 ml N,N-dimethylformamide) and water (100 ml) were added and the reaction mixture was rotated end-over-end at 4° C. for one hour. The resulting product was purified by chromatography using a NAP-10 column and phosphate buffered saline solution (pH 7.4) as the eluent. About 50 OD of product was obtained.

Part 3: Reaction of Derivatized Oligonucleotide with Enzyme Reagent

The activated oligonucleotide derivative described above (about 50 OD in 1.5 ml of phosphate buffered saline solution, pH 7.4) was added to the mercapto-substituted enzyme reagent prepared as described above (about 54 mg in 3.5 ml of buffered solution). The total volume was reduced to about 0.5 ml using an Amicon concentrator. The reaction mixture was then rotated end-over-end at 4° C. for 15 hours, followed by dilution to 5 ml with tris(hydroxymethyl)aminomethane buffer (0.02 molar, pH 8), and chromatographed on a DEAE-agarose column using as eluents: first with tris(hydroxymethyl)aminomethane buffer (pH 8), then with the buffer (0.02 molar) containing sodium chloride (1 molar). The fractions having an absorption ratio ($A_{260}/A_{403}$) of about 3.2 were combined and stored in phosphate buffered saline solution (pH 7.5) at a concentration of 1.5 OD/ml as the desired peroxidase-oligonucleotide covalent conjugate of this invention.

EXAMPLES 2-6: PREPARATION OF VARIOUS CONJUGATES

These examples were carried out like Example 1 using the same reagents and conditions to prepare various conjugates having different oligonucleotides. The oligonucleotides are listed as follows by their sequences ("U" represents uracil):

EXAMPLE 2

SEQ ID NO: 2:

5'-UTTTGGTCCT TGTCTTATGT CCAGAATGC-3'

EXAMPLE 3:

SEQ ID NO: 3

5'-TAGTAGCCAG CTGTGATAAA TGTCAGCTAA AAGGAGAAGC C-3'

EXAMPLE 4

SEQ ID NO: 4

5'-ACGGTACAGG CCAGACAATT ATTGTCTGGT ATAGT-3'

EXAMPLE 5

SEQ ID NO: 5
5'-GAGACCATCA ATGAGGAAGC TGCAGAATGG GAT-3'

EXAMPLE 6

SEQ ID NO: 6
5'-ATCCTGGGAT TAAATAAAAT AGTAAGAATG T-3'

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

---

We claim:

1. A method for preparing a covalent conjugate of an oligonucleotide and an enzyme comprising the steps of:

A. reacting an enzyme which has either a reactive amino group or a group that is convertible to a reactive amino group, with a blocked mercapto-substituted organic compound which is reactive with said reactive amino group through a condensation reaction, said organic compound having the structure:

R*—E—S—BLOCK wherein

R* is a group which is capable of reacting with said reactive amino group,

E is selected from the group consisting of $R^5$, $R^5—X'—R^6$, $X''—R^5$ and $X''—R^5—X'—R^6$, wherein $R^5$ and $R^6$ are independently alkylene or arylene and X' is oxy, thio or imino, and X'' is carbonyl, methylenecarbonyl, methylenecarbonyloxy, methylenecarbonylimino, ethylenesulfonyl, ethylenecarbonyl and methylenephenylene, and E has a molecular weight of from about 14 to about 1,000, and BLOCK is derived from a compound which is capable of reacting with said mercapto group o render said mercapto group non-nucleophilic, which BLOCK is subsequently removable, to form intermediate A' having the structure:

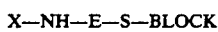

X—NH—E—S—BLOCK wherein X—NH— is said enzyme with a hydrogen atom removed from a reactive amino group, B. removing BLOCK from intermediate A' to form a reagent having the structure:

X—NH—E—SH,

C. providing an activated oligonucleotide derivative having the structure:

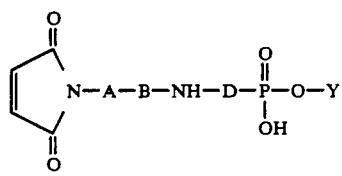

wherein:

A is selected from the group consisting of alkylene, arylene, cycloalkylene, heterocyclylene, and any combination of two or more of the foregoing divalent groups, B is selected from the group consisting of carbonyl, sulfonyl, oxycarbonyl, thiocarbonyl, iminocarbonyl and phospho, D is —D'—(—B'—)p- wherein D' is selected from the group consisting of heterocyclylene, $R^7$—(—O—$R^8$—)q- wherein $R^7$ and $R^8$ are independently alkylene or arylene, and any combination of two or more of the foregoing divalent groups, B' is selected from the group consisting of oxy, thio, imino, carbonylimino, iminocarbonyloxy, phosphonoxy and ureylene, p is 0 or 1, q is 1 to 30, and

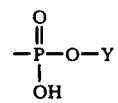

represents an oligonucleotide chain from which a hydroxy group has been removed from the terminal phosphate at the 3' or 5' end thereof, provided that —A—B—NH—D— has a molecular weight of from about 100 to about 10,000 daltons and D. reacting said activated oligonucleotide derivative provided in step C with the reagent formed in step B to form a conjugate having the structure:

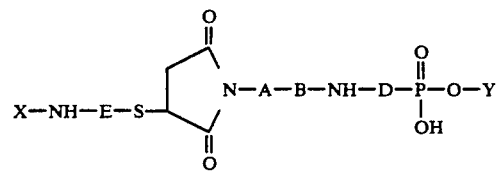

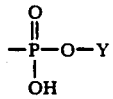

are as defined above.

2. The method of claim 1 wherein said enzyme is peroxidase, glucose oxidase, alkaline phosphatase or β-galactosidase.

3. The method of claim 1 wherein —BLOCK benzoyl, 2-carboxy-4-nitrophenylthio, triphenymethyl, pyridylcarbonyl or pyridylthio.

4. The method of claim 1 wherein BLOCK is acetyl.

5. The method of claim 1 wherein said oligonucleotide is attached to said conjugate at the 5' end thereof.

6. The method of claim 1 wherein:

A is a combination of two or more of said alkylene, arylene, cycloalkylene and heterocyclylene groups, B is carbonyl or oxycarbonyl, p is 1, D' is $R^7$—(—O—$R^8$—)q-, B' is oxy or thio, q is 1 to 15, and E is derived from a mercapto-protected alkylene anhydride.

7. The method of claim 6 wherein:

A is alkylenecycloalkylene of 7 to 14 carbon atom in the chain,

B is carbonyl,

B' is oxy,

D' is —D"—(—oxyalkylene—)q- wherein D" is alkylene of 1 to 6 carbon atoms, the alkylene of the oxyalkylene group has 2 to 12 carbon atoms.

8. A method for preparing a covalent conjugate of an oligonucleotide and an enzyme comprising the steps of:

A. reacting an enzyme having a reactive amino group with S-acetylmercaptosuccinic anhydride to form an intermediate having the structure:

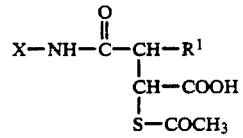

wherein

X—NH— represents said enzyme which has a reactive amino group from which a hydrogen atom has been removed, and $R^1$ is hydrogen, alkyl of 1 to 3 carbon atoms or hydroxyalkyl of 1 to 3 carbon atoms, B. reacting the intermediate formed in step A with hydroxylamine to form a reactive mercaptosubstituted intermediate having the structure:

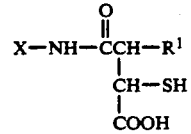

wherein X—NH— and $R^1$ are as defined above,

C. providing a functionalized oligonucleotide reactant having the structure:

E. reacting said activated oligonucleotide derivative formed in step D with the intermediate formed in step B to form a conjugate having the structure:

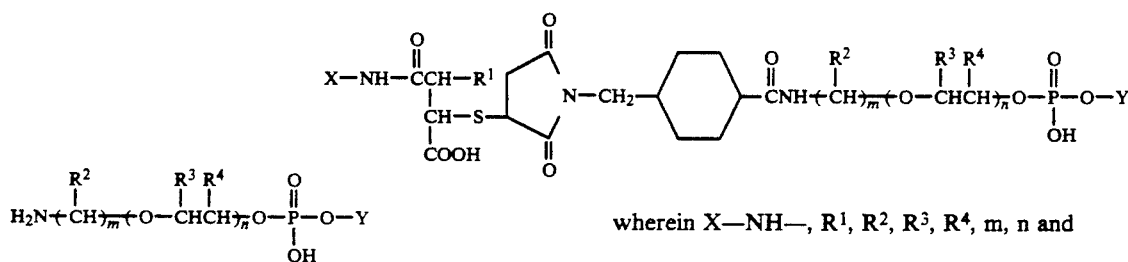

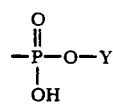

wherein

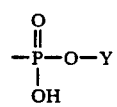

represents an oligonucleotide chain from which a hydroxy group has been removed from the terminal phosphate at the 5' end thereof, $R^2$, $R^3$ and $R^4$ are independently hydrogen, alkyl of 1 to 3 carbon atoms or hydroxyalkyl of 1 to 3 carbon atoms, m is a positive integer of 2 to 12, and n is a positive integer of 1 to 50, D. reacting said reactant provided in step C with sulfosuccinimidyl 4-(N-maleimidomethyl)cyclohexane-1-carboxylate to form an activated oligonucleotide derivative, and wherein X—NH—, $R^1$, $R^2$, $R^3$, $R^4$, m, n and $$-\overset{\overset{\displaystyle O}{\|}}{\underset{\underset{\displaystyle OH}{|}}{P}}-O-Y$$

are as defined above.

9. The method of claim 8 wherein $R^1$, $R^2$, $R^3$ and $R^4$ are independently hydrogen or methyl, m is 2, and n is 1 to 15.

10. The method of claim 8 wherein said enzyme is peroxidase and said oligonucleotide is attached at the 5' end thereof.

11. The method of claim 8 wherein said oligonucleotide has the following sequence SEQ ID NO:1:

5'-GAGTGATGAG GAAGAGGAGG GTG-3'.

12. The method of claim 8 wherein said oligonucleotide has the sequence selected from the group consisting of:

SEQ ID NO:2:

5'-UTTTGGTCCT TGTCTTATGT CCAGAATGC-3'

SEQ ID NO:3:

5'-TAGTAGCCAG CTGTGATAAA TGTCAGCTAA AAGGAGAAGC C-3'

SEQ ID NO:4:

5'-ACGGTACAGG CCAGACAATT ATTGTCTGGT ATAGT-3'

SEQ ID NO:5:

5'-GAGACCATCA ATGAGGAAGC TGCAGAATGG GAT-3'

SEQ ID NO:6:

5'-ATCCTGGGAT TAAATAAAAT AGTAAGAATG T-3'.

* * * * *